United States Patent
Gigioli et al.

(10) Patent No.: US 7,525,660 B2
(45) Date of Patent: Apr. 28, 2009

(54) SYSTEMS AND METHODS FOR USE IN DETECTING HARMFUL AEROSOL PARTICLES

(75) Inventors: George W. Gigioli, Brookeville, MD (US); David W. Bope, Burtonsville, MD (US); Peter P. Hairston, Severna Park, MD (US); Edward A. Miller, Severna Park, MD (US)

(73) Assignee: Northrop Grumman Systems Corporation, Los Angeles, CA (US)

( * ) Notice: Subject to any disclaimer, the term of this patent is extended or adjusted under 35 U.S.C. 154(b) by 0 days.

(21) Appl. No.: 11/755,535

(22) Filed: May 30, 2007

(65) Prior Publication Data

US 2008/0002180 A1  Jan. 3, 2008

Related U.S. Application Data

(63) Continuation-in-part of application No. 11/349,341, filed on Feb. 8, 2006.

(60) Provisional application No. 60/650,521, filed on Feb. 8, 2005.

(51) Int. Cl.
*G01N 21/64* (2006.01)
(52) U.S. Cl. .................. 356/417; 250/461.1
(58) Field of Classification Search ............. 356/416, 356/417; 250/226, 461.1
See application file for complete search history.

(56) References Cited

U.S. PATENT DOCUMENTS

| | | | |
|---|---|---|---|
| 4,164,373 A | 8/1979 | Schuss et al. | |
| 4,405,199 A | 9/1983 | Ogle et al. | |
| 4,573,796 A | 3/1986 | Martin et al. | |
| 4,657,398 A | 4/1987 | Brunsting | |
| 5,288,995 A | 2/1994 | Strachan | |
| 5,739,902 A * | 4/1998 | Gjelsnes et al. | 356/73 |
| 5,751,429 A | 5/1998 | Wada | |
| 5,760,900 A | 6/1998 | Ito et al. | |
| 5,828,452 A | 10/1998 | Gillispie et al. | |
| 6,249,341 B1 | 6/2001 | Basiji et al. | |
| 6,266,139 B1 | 7/2001 | Mannhardt | |
| 6,473,176 B2 | 10/2002 | Basiji et al. | |
| 6,592,822 B1 | 7/2003 | Chandler | |
| 6,671,044 B2 * | 12/2003 | Ortyn et al. | 356/326 |
| 6,787,104 B1 * | 9/2004 | Mariella, Jr. | 422/4 |
| 6,885,440 B2 * | 4/2005 | Silcott et al. | 356/73 |
| 7,015,484 B2 | 3/2006 | Gillispie et al. | |
| 7,064,827 B2 | 6/2006 | Nurmikko et al. | |
| 7,106,442 B2 | 9/2006 | Silcott et al. | |
| 7,116,407 B2 | 10/2006 | Hansen et al. | |
| 7,123,416 B1 * | 10/2006 | Erdogan et al. | 359/589 |
| 2002/0030812 A1 | 3/2002 | Ortyn et al. | |
| 2002/0093641 A1 | 7/2002 | Ortyn et al. | |

(Continued)

OTHER PUBLICATIONS

Office Action issued in U.S. Appl. No. 11/349,340 on Jun. 6, 2007, 22 pp.

(Continued)

*Primary Examiner*—F. L Evans
(74) *Attorney, Agent, or Firm*—Rothwell, Figg, Ernst & Manbeck

(57) ABSTRACT

The invention provides systems and methods for detecting aerosols. The systems and methods can be used to detect harmful aerosols, such as, bio-aerosols.

34 Claims, 10 Drawing Sheets

U.S. PATENT DOCUMENTS

| | | |
|---|---|---|
| 2002/0094116 A1 | 7/2002 | Frost et al. |
| 2002/0094166 A1 | 7/2002 | Weerden et al. |
| 2003/0235919 A1 | 12/2003 | Chandler |
| 2004/0007675 A1 | 1/2004 | Gillispie et al. |
| 2004/0223135 A1 | 11/2004 | Ortyn et al. |
| 2005/0036139 A1 | 2/2005 | Johnson |
| 2005/0105077 A1 | 5/2005 | Padmanabhan et al. |
| 2005/0162648 A1* | 7/2005 | Auer et al. .................. 356/318 |
| 2006/0238757 A1* | 10/2006 | Silcott ........................ 356/338 |

OTHER PUBLICATIONS

Office Action issued in U.S. Appl. No. 11/349,341 on Jun. 15, 2007, 20 pp.

Office Action issued in U.S. Appl. No. 11/349,344 on Jun. 15, 2007, 20 pp.

International Search Report and Written Opinion issued in PCT/US06/04279 on Sep. 26, 2007, 16 pp.

* cited by examiner

SYSTEMS AND METHODS FOR USE IN DETECTING HARMFUL AEROSOL PARTICLES

This application is a continuation-in-part of U.S. patent application Ser. No. 11/349,341, filed on Feb. 8, 2006, which claims the benefit of U.S. Provisional Patent Application No. 60/650,521, filed on Feb. 8, 2005. The above referenced applications are incorporated herein by this reference.

BACKGROUND OF THE INVENTION

1. Field of the Invention

The invention generally relates to systems and methods for, inter alia, detecting harmful aerosol particles, and, in some embodiments, to multi-spectral aerosol particle measurement systems.

2. Discussion of the Background

Aerosol particles (or aerosols) are particles that are suspended in a gas (e.g., the air we breathe). Some aerosol particles may be harmful to humans. Thus, there is a need to detect the presence of harmful aerosol particles in an area in which humans are present.

SUMMARY OF THE INVENTION

The present invention provides systems and methods for, among other things, detecting the presence of harmful or other aerosol particles, such as, for example, biological aerosols.

An aerosol detector system according to one embodiment of the invention includes: a detector having a detector input and a field of view; an emitter apparatus configured to emit into a region of space within the field of view of the detector different wavelengths of excitation energy at different times such that a particle located within the field of view of the detector may be exposed to said different wavelengths of excitation energy at said different times; and a filter disposed in front of the detector input, wherein the filter is configured to filter a first band of wavelengths and a second band of wavelengths. Preferably, the detector system includes only the detector and no other detectors.

In some embodiments, the first band of wavelengths includes wavelengths less than 320 nm and the second band of wavelengths includes wavelengths between 370 and 420 nm. The filter may include a single filter substrate having a first filter coating on one side and a second filter coating on the other side, wherein the first filter coating filters wavelengths less than the first wavelength, and the second filter coating filters wavelengths less than the third wavelength, but not less than the second wavelength. The emitter apparatus may include a laser operable to emit excitation energy having a wavelength of less than 320 nm. In other embodiments, the emitter apparatus includes: (a) a first emitter configured to emit excitation energy having a wavelength of less than 320 nm and (b) a second emitter configured to emit excitation energy having a wavelength of less than 420 nm but greater than 370 nm.

An aerosol detection method according to one embodiment of the invention includes the following steps: (a) while an aerosol is positioned within a field of view of a detector, illuminating the aerosol using a first wavelength of light; and (b) after performing step (a) and while the aerosol is still positioned within the field of view of the detector, illuminating the aerosol using a second wavelength of light, wherein a filter is disposed between the aerosol and an input of the detector so that light emitted from the aerosol must pass through the filter prior to reaching the input of the detector, and the filter is configured to filter a first band of wavelengths and a second band of wavelengths.

The step of illuminating the aerosol using the first wavelength of light may consist of illuminating the aerosol with the first wavelength of light for a short period of time, and the step of illuminating the aerosol using the second wavelength of light may consist of illuminating the aerosol with the second wavelength of light for a short period of time. Additionally, the first band of wavelengths may include the first wavelength and the second band of wavelengths may include the second wavelength. The first wavelength may be less than 320 nm and the second wavelength may be between 370 nm and 420 nm.

The method may also include: obtaining a first signal output from the detector and processing the first signal, wherein the first signal corresponds to the intensity of light emitted from the aerosol in response to the aerosol being illuminated by the first wavelength, obtaining a second signal output from the detector and processing the second signal, wherein the second signal corresponds to the intensity of light emitted from the aerosol in response to the aerosol being illuminated by the second wavelength, and determining whether the aerosol is a harmful aerosol based, at least in part, on said first signal and said second signal.

The above and other features and/or advantages of embodiments of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, help illustrate various embodiments of the present invention and, together with the description, further serve to explain the principles of the invention and to enable a person skilled in the pertinent art to make and use embodiments of the invention. In the drawings, like reference numbers indicate identical or functionally similar elements.

DETAILED DESCRIPTION OF PREFERRED EMBODIMENTS

Figure 1:
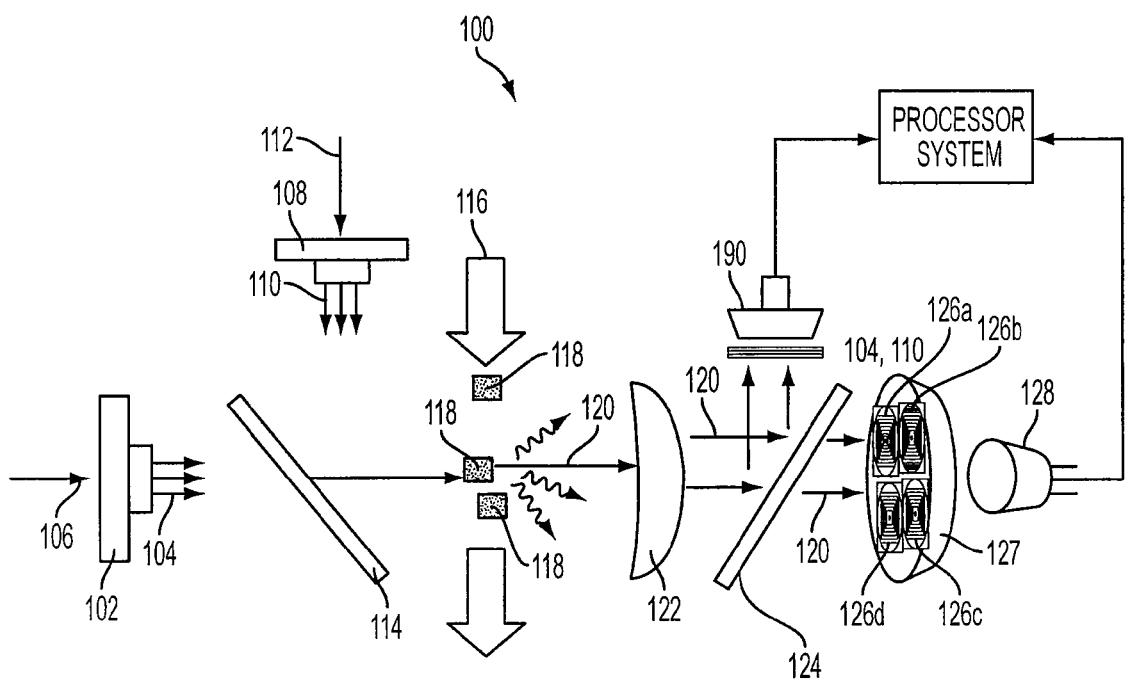
FIG. 1 is a schematic of a system according to a first embodiment of the invention.

As used herein, the term "a" means "one or more," unless expressly noted otherwise.

One widely accepted method of discriminating particles of biological nature in nearly real time is through measurement of intrinsic fluorescence of airborne particles. Using this method, potential biological threat agents, such as anthrax or drug content within inert carrier materials from a nebulizer, may be distinguished from benign "background" particles normally present in ambient air.

Biological threat particles such as bacteria, toxins, and viruses contain a variety of fluorophores that can be used to discriminate or characterize the particles. The primary fluorophores include tryptophan, NADH, flavins, dipicolinic acid, phenylalanine, tyrosine, and other proteins. In addition, residues from the production of biological threat particles can indicate the manufacture of biological threats. Examples of these residues are growth media and bacteria used as hosts for bacterial phage viruses.

Fluorophores have characteristic excitation and emission spectra. The emission spectra generally span several tens or hundreds of nanometers of wavelength, and may overlap. Background particles that are not of interest for a specific detection requirement may have fluorescence characteristics of their own.

The fluorescence characteristics of the background particles may be similar to some, but usually not all, of that of the fluorophores in particles that are of interest as targets for detection. The fluorescence of the fluorophores targeted for detection may thus overlap that of the background particles.

Background particles may also have additional fluorescence properties that are distinct from that of the target particles. Fluorescence measurements that are indicative of background particles may also be useful in discriminating background particles from particles that are targets for detection.

Aerosol particle fluorescence measurements are typically performed on a continuous basis. In an aerosol particle fluorescence measurement, radiation of various wavelengths is directed at a flowing fluid that contains particles, causing the particles to produce fluorescent radiation at wavelengths that are characteristic of the particles. Measurement of individual particles, as opposed to aggregates of particles, provides better discrimination of target particles in a background, since each individual measurement is made on either a target particle or a background particle without commingling of the measurements.

Aerosol fluorescence measurements do not typically incur any operating costs other than the electrical power necessary to run an emitter, a detector, and control circuitry. Aerosol particle fluorescence measurements are thus often used to indicate the possibility of threat particles.

In this way, aerosol fluorescence measurements can be used as an initial fast screening tool. If the aerosol particle fluorescence measurement gives a positive indication of a threat, it may be followed by slower, more costly measurements to confirm or refute the initial threat indication.

Since there are multiple biological and background particle fluorophores, more specific indicators of biological threats or other fluorescent characteristics of particles may be necessary. Fluorescence measurements can be made more specific by increasing the number excitation and emission wavelength regions that are used.

When multiple excitation wavelengths are used, various wavelengths may be sequenced in time, or separated in space, or both. Separating excitation wavelengths in time or space avoids confounding emissions stemming from one excitation with emissions stemming from a different excitation.

Additional specificity for the classification of fluorescent particles can be gained by measurement of light scatter or aerodynamic particle size along with the fluorescence measurements.

The fluorescence emitted by a single particle or from a volume of aerosol may be of low intensity. If the fluorescence is distributed among too many emission detection channels, the amount of detectable fluorescent light (or number of photons) per channel may provide an insufficient per-channel signal-to-noise ratio. If the signal-to-noise ratio of a channel is small, it may be difficult to provide a useful correlation among signals detected from identical input particles.

A system that measures multiple emissions, including multiple emissions from multiple excitation wavelengths, may be expensive and complex. Such a system may require a separate detector for each emission wavelength region.

Photomultiplier tube detectors costing hundreds of dollars are typically necessary for the low optical signal levels typical of biological aerosol particles. While multi-element detectors such as multi-channel plates, image intensifiers, and multi-segment photomultipliers could also be used, these are all relatively expensive when suited to the needed sensitivity and bandwidth.

If a single detector were used, the cost and complexity associated with multiple detectors could be avoided. At least some embodiments described herein reduce the cost and complexity of particle characterization systems by using only a single detector to detect multiple wavelength bands of fluorescence emissions from a particle or aerosol, or, more generally, they use a number of detectors that is fewer than the number of wavelength channels detected.

It should be noted that these methods may be applied to other fluorescence measurement applications, such as for particles in any fluid, with hydrosols in a flow cytometer being one example. Further, these concepts may also be applicable to other excitation emission wavelength based optical measurements, such as measuring Raman emissions and laser-induced breakdown emissions.

In a system with multiple detectors, it is possible to detect multiple fluorescence channels simultaneously. A system with multiple detectors may thus acquire a complete set of emission spectral information from a single particle.

A single detector system, on the other hand, obtains a single wavelength or color band from any given particle measurement. For applications such as detection of biological threat aerosols, however, the aerosol cloud will be present for several seconds or more. Thus, particles measurements may be taken serially over a selection of color band settings within the time that the aerosol cloud is present. The fluorescence characteristics that are then measured will provide more complete information about the particles within the cloud and enhance discrimination of particle types.

FIG. 1 is a schematic of a multi-spectral aerosol particle measurement system 100 according to a first embodiment of the invention. As shown in FIG. 1, a multi-spectral aerosol particle measurement system 100 may include a long emitter 102 emitting long wavelength radiation 104 (e.g., UV light at approximately 340 nm) in a first direction 106 and a short emitter 108 emitting short wavelength radiation 110 (e.g., UV light at approximately 280 nm) in a second direction 112 (direction 112 may be orthogonal to direction 106 as illustrated in FIG. 1).

An emitter reflector 114 may be positioned at an intersection of first direction 106 and second direction 112 to pass long wavelength radiation 104 in first direction 106 and reflect short wavelength radiation 110 in first direction 106. In one embodiment, emitter reflector 114 is a filter, such as a dichroic filter, that is transparent to long wavelength radiation 104 and reflective to short wavelength radiation 110. In another embodiment, emitter reflector 114 comprises a plurality of filters that can be used sequentially to produce various bands of long wavelength radiation 104 and short wavelength radiation 110.

A flowing fluid 116 that contains particles may intersect first direction 106 such that the particles in fluid 116 (or "particle stream 116") are sequentially exposed to both long wavelength radiation 104 and short wavelength radiation 110. A particle 118 in particle stream 116 intersecting first direction 106 may produce elastic and inelastic emission wavelengths (the inelastic emission wavelengths may include a fluorescent radiation 120 resulting from the particle's exposure to either the long wavelength radiation or the short wavelength radiation, sequentially, or both) when exposed to the long or short wavelength radiation 104, 110.

A collimating lens 122 positioned in first direction 106 may receive and collimate long and short wavelength radiation 104, 110 and fluorescent radiation 120. A detector reflector 124 (e.g., a dichroic filter or the like) positioned in first direction 106 may reflect short wavelength radiation and pass fluorescent radiation 120 so that it passes through at least one a plurality of detector filters 126a-d. Each of detector filters 126a-d may be placed in the optical detection path of a detector 128.

In one embodiment, detector filters 126a-d may be disposed in a holder 127. Holder 127 may be mechanically moved (e.g., rotated) in a controlled manner to position different detector filters 126a-d in the optical path of detector 128. The sequencing of detector filters 126a-d may be combined with the sequencing of two, as shown, or more excitation sources.

In one embodiment, filter 124 reflects light having a wavelength shorter than 300 nm so that elastic scatter caused by a particle exposed to, for example, a 280 nm radiation source is detected by light scatter detector 190, and it's amplitude measured by the a data processor (e.g., a signal processor or other data processor). Further, filter 126A is configured to pass 400-500 nm fluorescence from the particle exposed to a 340 nm light, while filter 126B is configured to pass 320-400 nm fluorescence from the particle when it is exposed to 280 nm light.

After measuring at least one particle, but typically after measuring a number of particles greater than 100, or after measuring particles for a fixed time interval (e.g., 1 second), filter holder 127 is moved (e.g., rotated) to a second position, such that 500-600 nm fluorescence is measured when a particle is in the 340 nm light, and 400-500 nm fluorescence is measured when the particle is in the 280 nm light. An example sequence of operation is summarized as: Filter setting 1 measurements: 280 nm light scatter, 400-500 nm fluorescence from 340 nm source, 300-400 nm fluorescence from 280 nm source; Filter setting 2 measurements: 280 nm light scatter, 500-600 nm fluorescence from 340 nm source, 400-500 nm fluorescence from 280 nm source.

In one embodiment, long emitter 102 and short emitter 108 may be paired with each detector filters 126a-d in turn to detect various fluorophores. In one embodiment, a controller (e.g., a computer or other control system) may be used to switch long emitter 102 and short emitter 108 on and off while each of four detector filters 126a-d are positioned in first direction 106.

A fluorescence emission band of interest excited by short emitter 108 may partly correspond to wavelength 104 of long emitter 102. In this embodiment, light scatter from long emitter 102, rather than fluorescent radiation 120, can be measured at one of the detector filter 126 sequence settings.

In general it is advantageous to obtain a scattered light intensity simultaneously with, or corresponding to, each fluorescence measurement. This allows particles to be differentiated based on their fluorescence to light scatter ratios. Fluorescence to light scatter ratios may be indicative of the concentration or quantum efficiency of the fluorophores in particle stream 116.

In an alternative embodiment, it could be advantageous to include more than one filter at each of detector filters 126a-d. In this embodiment, the combined response of two filters, such a long pass filter combined with a short pass filter, could be used to create a band pass filter.

In another embodiment, a filter 126 may include or consist of a diffraction grating or a prism. In this embodiment, the diffraction grating or prism could be tilted sequentially to deliver a different portion of the spectrum to detector 128.

In another embodiment, a filter 126 may include or consist of an electrically or acoustically tunable filter, such as a MEMS based device. The optical and mechanical configuration of such tunable filters can be arranged to provide sequentially any selected wavelength regions of the collected emission to detector 128.

Figure 2:
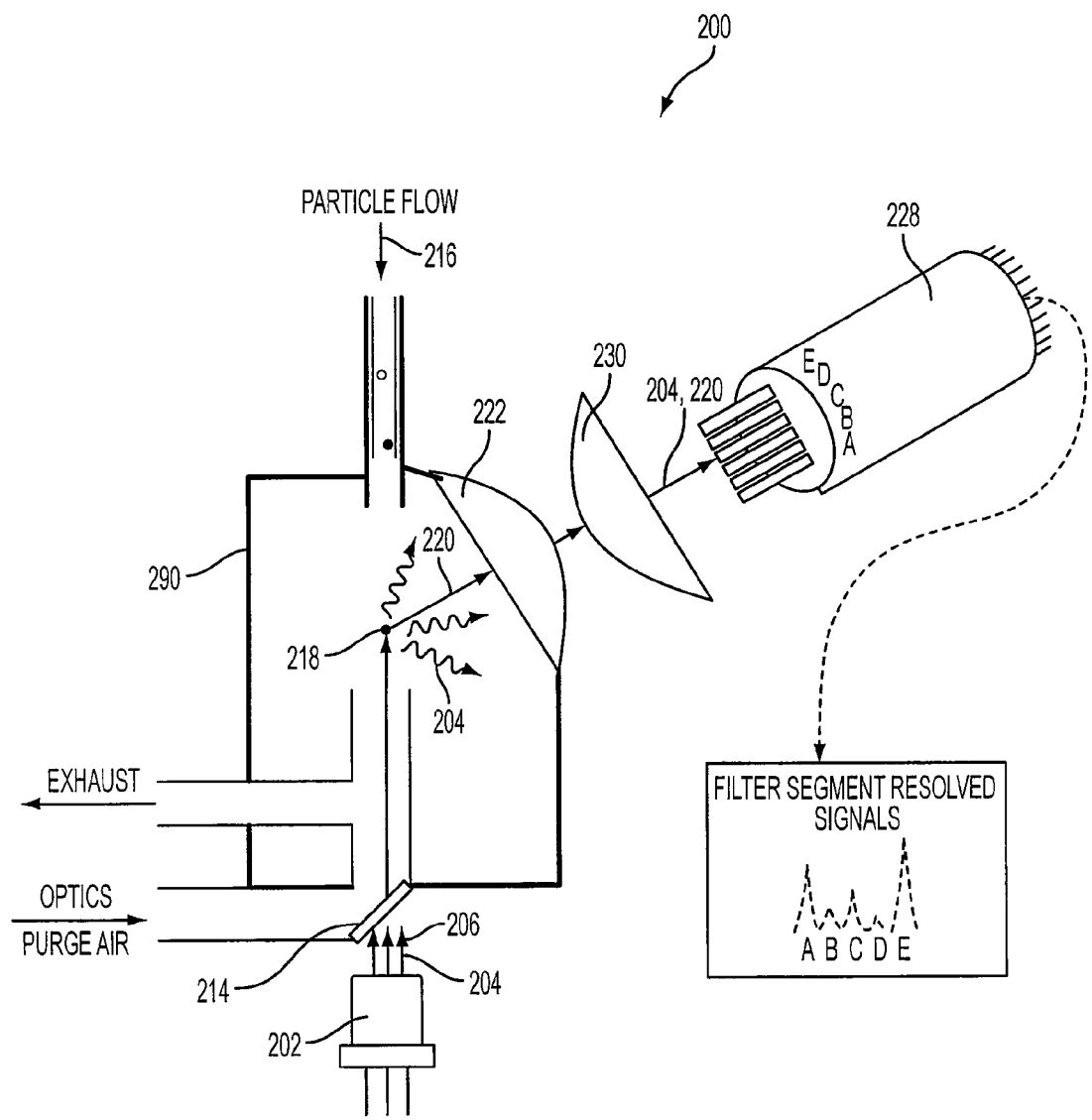
FIG. 2 is a schematic of a system according to a second embodiment of the invention.

FIG. 2 is a schematic of a multi-spectral aerosol particle measurement system 200 according to a second embodiment of the invention. As shown in FIG. 2, multi-spectral aerosol particle measurement system 200 may include a long emitter 202 emitting in a first direction 206 long wavelength radiation 204 (e.g., light having a wavelength of about 375 nm). A window 214, kept clean by a filtered purge air flow, allows radiation 204 to enter an optical chamber 290.

A fluid flow 216 containing particles ("particle stream 216") may traverse first direction in a direction substantially opposite to that of long wavelength radiation 204. A particle 218 in stream 216 may produce fluorescent radiation 220 when exposed to radiation 204. An optical apparatus, which may include a collimating lens 222 and a focusing lens 230, may be positioned to receive and collimate fluorescent radiation 220, as well as long wavelength radiation 204 that has been scattered.

The focusing lens 230 may be positioned to receive and focus collimated radiation 204 and fluorescent radiation 220. A detector 228 may be placed at a focus of focusing lens 230 to receive elastic scatter and fluorescent radiation 220. Accordingly, the optical apparatus may be configured to direct the radiation 220 and scatter to the detector.

In one embodiment, detector 228 may be a photomultiplier tube with a sufficiently large photosensitive area for there to be multiple filters A, B, C, D, and E positioned in front of detector 228. In one embodiment, it may be advantageous for signal separation to have opaque strip separating each filter A, B, C, D, and E.

In several embodiments (including similar alternative embodiments), collimating lens 222 and focusing lens 230 may be reflective or refractive optics (e.g., spherical, ellipsoidal, or parabolic reflectors). In several embodiments, an optical fiber or a light pipe may be used to transmit long wavelength radiation 204 to particle stream 216.

In this embodiment, measurements may be obtained from multiple wavebands of fluorescent radiation 220 produced by a single particle 218. In this embodiment, fluorescent radiation 220 produced by single particle 218 is directed or "imaged" onto array of filters A, B, C, D, and E of detector 228 as particle 218 moves in particle stream 216. In a preferred embodiment, the array of filters together covers the range of fluorescence and light scatter produced by target particles and background particles to be differentiated. For 375 nm excitation, a preferred series of filters is: A=550-600 nm, B=500-550 nm, C=450-500 nm, D=400-450 nm, E=<400 nm, with E including elastically scattered light. In this embodiment, fluorescent radiation 220 produced by single particle 218 is directed or imaged sequentially through each of filters A, B, C, D, and E. This is illustrated in FIG. 8.

Figure 8:
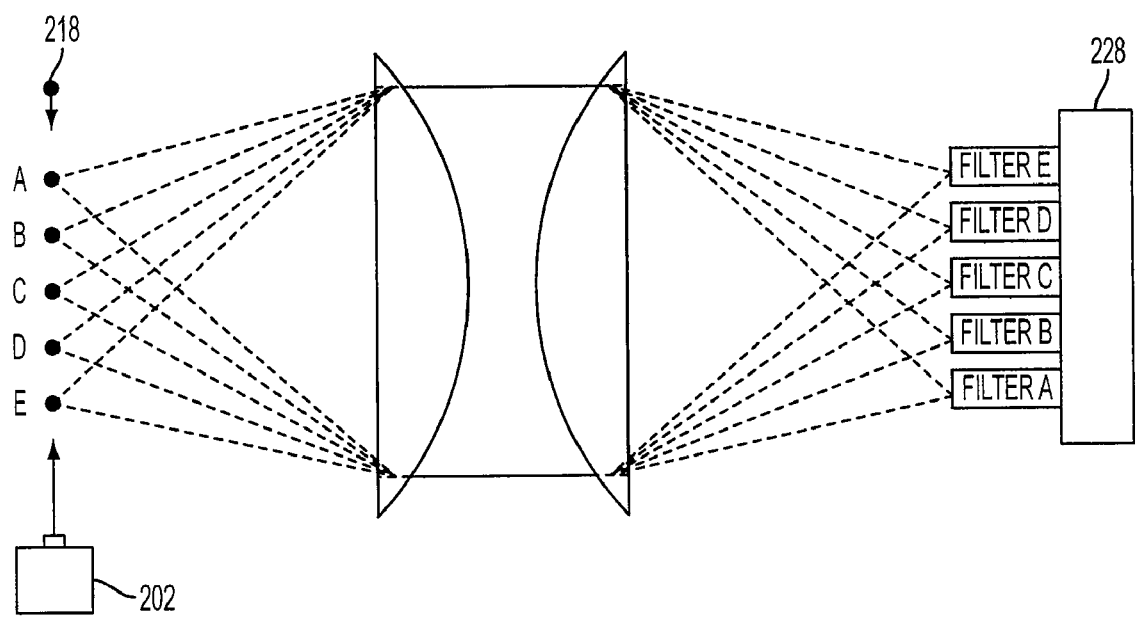
FIG. 8 illustrates a particle moving from a point A to a point E through points B-D.

FIG. 8 illustrates particle 218 moving from point A to point E through points B-D. When particle 218 is located at or near point A, the elastic and inelastic emission wavelengths produced by particle 218, which emission wavelengths are produced as a result of particle 218 receiving radiation 204, pass only or primarily through a single filter (e.g., filter A). Similarly, at a later point in time, when particle 218 is located at or near point B, the emission wavelengths produced by particle 218 pass only or primarily through a single filter (e.g., filter B). Likewise, at a still later point in time, when particle 218 is located at or near point C, D or E, the emission wavelengths produced by particle 218 pass only or primarily through a single filter (e.g., filter C, D or E, respectively). Thus, in this manner, fluorescent radiation 220 produced by single particle 218 may be directed or imaged sequentially through each of filters A, B, C, D, and E.

As illustrated in FIG. 8, by employing two or more filters between the particle and a single detector, it is possible to use only a single detector to detect elastic and multiple inelastic emission wavelengths from an individual particle that, while moving from one point to another, is exposed to an excitation wavelength. In several embodiments, multi-element photomultipliers, micro channel plates, or image enhanced charge coupled devices (CCD's) could also accomplish multispectral sensing. In other words, embodiments of the present invention enable one to create a detection system wherein the number of detectors is less than the number of emission wavelengths detected. This is advantageous because, typically, the most costly components of a detection system are the detectors themselves.

Figure 3:
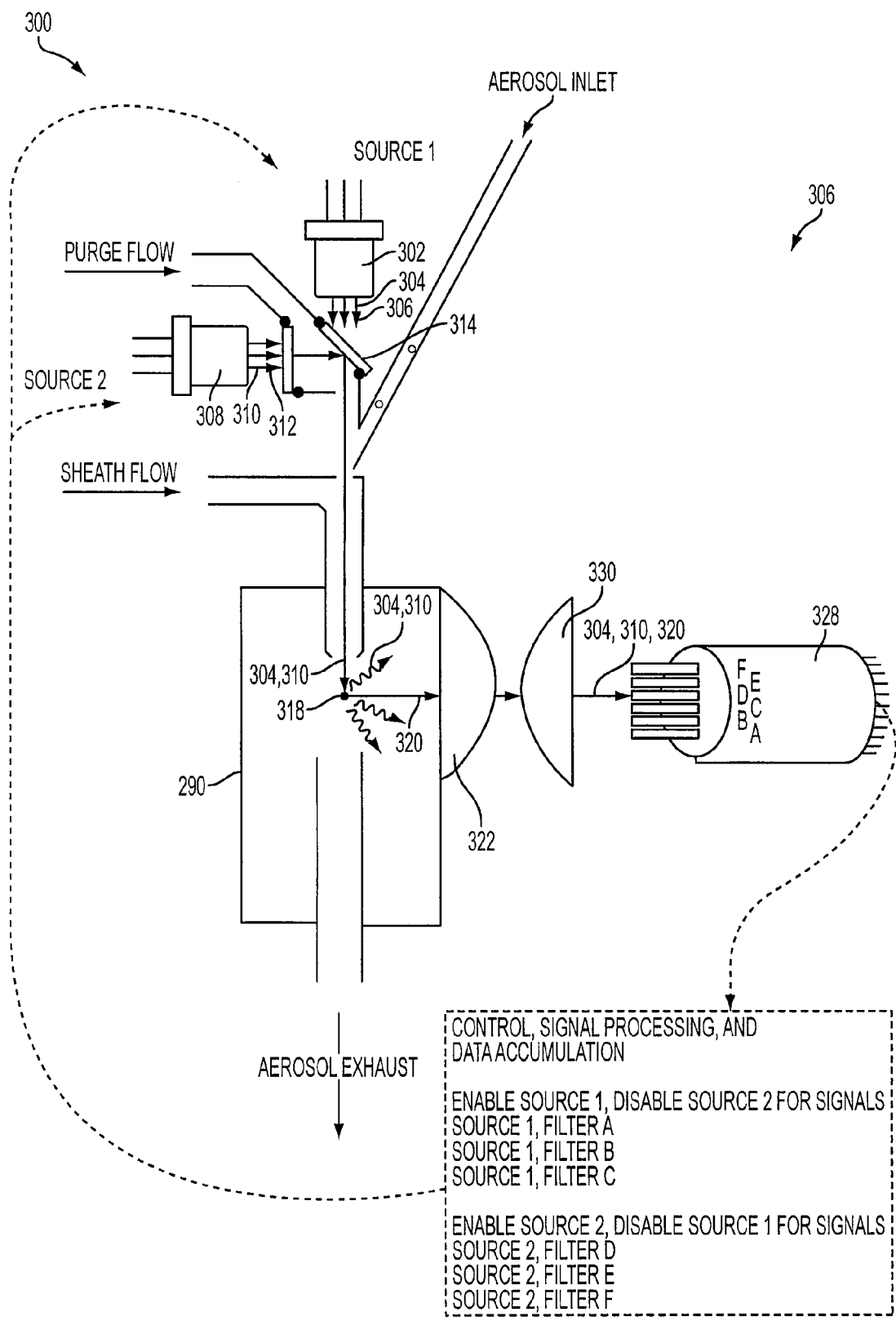
FIG. 3 is a schematic of a system according to a third embodiment of the invention.

FIG. 3 is a schematic of a multi-spectral aerosol particle measurement system 300 according to a third embodiment of the invention. As shown in FIG. 3, multi-spectral aerosol particle measurement system 300 may include a long emitter 302 emitting in a first direction 306 long wavelength radiation 304 (e.g., light having a wavelength of about 405 nm) and a short emitter 308 emitting in a second direction 312 short wavelength radiation 310 (e.g., light having a wavelength of about 280 nm).

An emitter reflector 314 (e.g., a dichroic mirror) may be placed at an intersection of first direction 306 and second direction 312 to pass long wavelength radiation 304 in first direction 306 and reflect short wavelength radiation 310 in first direction 306. In one embodiment, emitter reflector 314 comprises a plurality of filters (not shown) that can be used to produce three or more different wavelength bands of radiation. Reflector 314 may be the same as reflector 124 described above.

A particle 318 in a fluid flow may travel along first direction 306 such that particle traverses along in the locations of both long wavelength radiation 304 and short wavelength radiation 310. The particle 318 may produce radiation at a fluorescent wavelength radiation 320 when exposed to long or short wavelength radiation 304, 310.

A collimating lens 322 may be positioned to receive and collimate fluorescent radiation 320 as well as scattered long and short wavelength radiation 304, 310. A focusing lens 330 may be positioned to receive and focus collimated long or short wavelength radiation 304, 310 and fluorescent radiation 320.

A detector 328 may be positioned at a focus of focusing lens 330 to receive long or short wavelength radiation 304, 310 and fluorescent radiation 320. In one embodiment, detector 328 may be a photomultiplier tube with a sufficiently large photosensitive area for there to be multiple filters A, B, C, D, E and F positioned in front of detector 328.

In some embodiments, collimating lens 322 and focusing lens 330 may be reflective or refractive optics (e.g., spherical, ellipsoidal, or parabolic reflectors). In some embodiments, an optical fiber or a light pipe may be used to transmit long and short wavelength radiation 304 and 310.

In this embodiment, long and short wavelength radiation 304, 310 are different but overlapped spatially, and are switched on for alternate time intervals.

For example, long emitter 302 would emit into a predefined region of space and for a first time interval long wavelength radiation 304, during which time interval the particle 318 moves through at least a first portion of the region of space in which the radiation 304 is present, thereby exposing the particle to the radiation 304. As the particle 318 moves through the first portion of the region, emissions caused by the particle's exposure to the radiation may be produced. These emissions may be sequentially approximately focused onto filters A, B and then C.

After the first time interval and while the particle 318 is still located within the region, long emitter 302 ceases emitting radiation 304 and short emitter 308 would be switched on to emit short wavelength radiation 310 into the region for a second time interval, during which second time interval the particle 318 moves through at least a second portion of the region of space in which the radiation 310 is present, thereby exposing the particle to radiation 310. As the particle 318 moves through the second portion of the region, emissions caused by the particle's exposure to radiation 310 may be produced. These emissions may be sequentially approximately focused onto filters D, E and then F.

For 405 and 280 nm emitters, one preferred selection of filters is: A=<420 nm with partial attenuation of 405 nm such that the scattered 405 nm light can be measured at the same detector gain as the weaker fluorescence signals excited by 405 nm; B=430-500 nm (fluorescence excited by 405 nm); C=500-600 nm (fluorescence excited by 405 nm); D=310-380 nm (fluorescence excited by 280 nm); E=430-500 nm (fluorescence excited by 280 nm); F=<300 nm with partial attenuation of 280 nm such that the scattered 280 nm light is can be measured at the same detector gain as the weaker fluorescence signals excited by 280 nm.

FIG. 2 shows radiation 204 being emitted along direction 206 which is the opposite direction in which the fluid containing particle 218. This may provide approximately uniform illumination of particle 218 as it flows through the excitation region. This may further allow sub-regions of the fluid to be imaged easily to detector filter array A, B, C, D, E, and F. However, the concept of using a sequentially positioned filter array A, B, C, D, E, and F may be applied regardless of the direction from which the excitation radiation arrive at the fluid flow.

Figure 4:
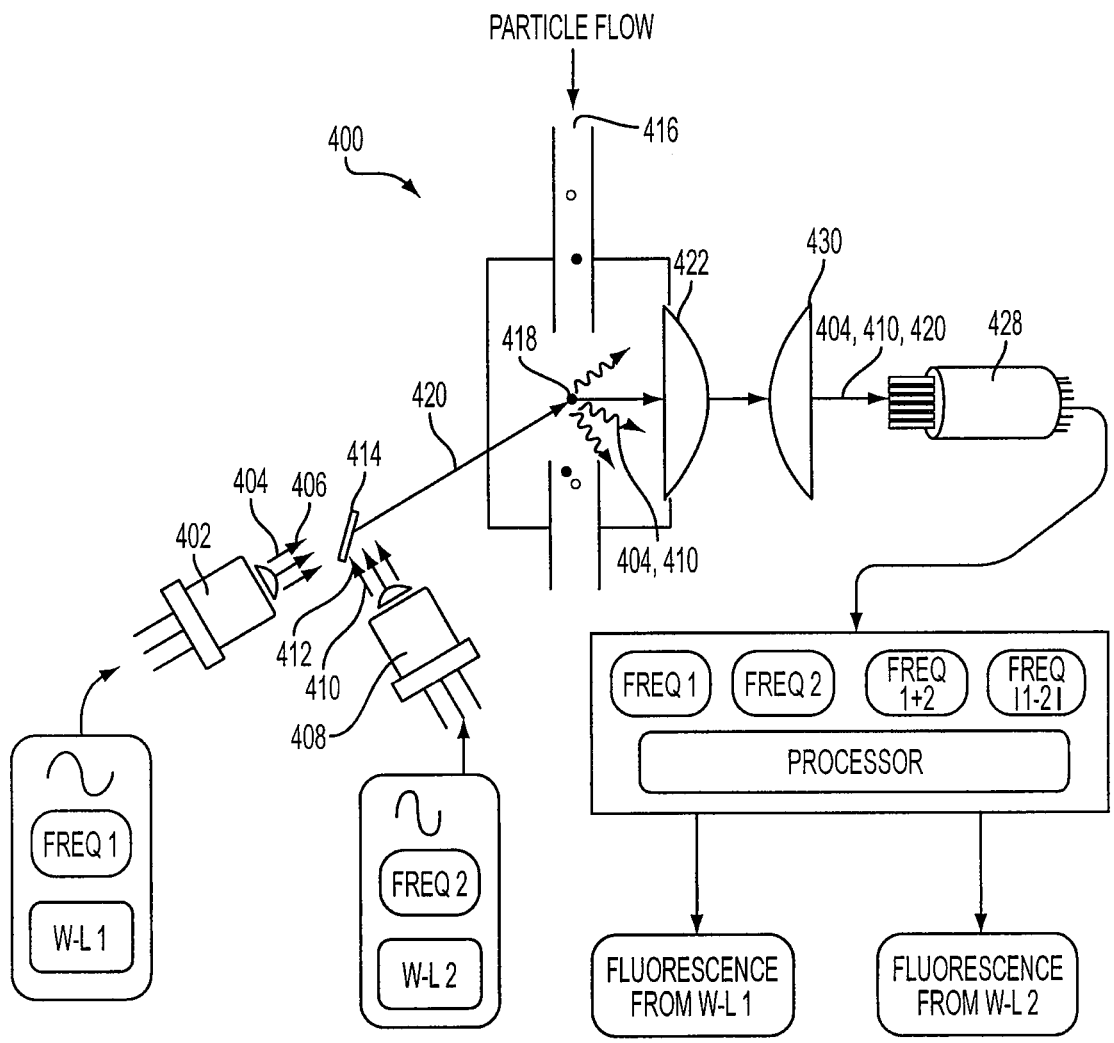
FIG. 4 is a schematic of a system according to a fourth embodiment of the invention.

FIG. 4 is a schematic of a multi-spectral aerosol particle measurement system 400 according to a fourth embodiment of the invention. As shown in FIG. 4, multi-spectral aerosol particle measurement system 400 may include a long emitter 402 emitting in a first direction 406 long wavelength radiation 404 (e.g., light having a wavelength of about 340 nm) and a short emitter 408 emitting in a second direction 412 short wavelength radiation 410 (e.g., light having a wavelength of about 280 nm).

An emitter reflector 414 may be placed at an intersection of first direction 406 and second direction 412 to pass long wavelength radiation 404 in first direction 406 and reflect short wavelength radiation 410 in first direction 406. Emitter reflector may be the same as reflector 314 or 124.

A flowing fluid 416 containing particles (e.g., particle 418) may intersect first direction 406. Radiation 404 or radiation 410 may strike particle 418, causing particle 418 to produce fluorescent wavelength radiation 420. A collimating lens 422 may be positioned to receive and collimate fluorescent radiation 420, as well as scattered long and short wavelength radiation 404, 410.

A focusing lens 430 may be positioned to receive and focus collimated long and short and fluorescent radiation 420. A detector 428 may be positioned at a focus of focusing lens 430 to receive long and short wavelength radiation 404, 410 and fluorescent radiation 420. In one embodiment, detector 428 may be a photomultiplier tube.

In several embodiments, collimating lens 422 and focusing lens 430 may be reflective or refractive optics (e.g., spherical, ellipsoidal, or parabolic reflectors). In several embodiments, an optical fiber or a light pipe may be used to transmit long and short wavelength radiation 404 and 410 to particle stream 416.

In this embodiment, both long emitter 402 and short emitter 408 illuminate particles in fluid 416 with long wavelength radiation 404 and short wavelength radiation 410, respectively. In one embodiment, long emitter 402 and short emitter 408 are modulated at different frequencies.

In this embodiment, long wavelength radiation 404 and short wavelength radiation 410 scatter may be distinguished from fluorescent radiation 420 at detector 428 by analyzing the frequency components of emitted radiation at detector 428. In one embodiment, the modulation frequencies may be significantly higher than the reciprocal of a transit time of particle 418 through long wavelength radiation 404 and short wavelength radiation 410, and may be in the range of 1 to 100 MHz.

In one embodiment, the contribution to the signal produced by detector 428 due to long emitter 402 and short emitter 408 are determined. In this embodiment, the spectral power of the signal at detector 428 could be analyzed at each of the modulation frequencies.

As illustrated in FIG. 4, two or more excitation wavelengths may be superimposed on each other, and each source modulated at different frequency (e.g., in the 1 KHz to 1 GHz range), with each frequency providing 10 or more cycles during the transit time of a particle through the region of space in which the particle is illuminated by the excitation wavelengths. A portion of the inelastic and elastic scatter signals are transmitted by reflective or refractive optics to a detector through a filter or combination of filters that selects the spectra of interest (and may selectively reduce the intensity of the some wavelengths to allow all selected wavelength signals to be detected within the useful linear response region of the detector). The detector output is then a combination of frequencies determined by the modulation frequencies of each source. The optical emission wavelength region determined by the filter or filter combination and corresponding to each source is then determined by Fourier or other electronic spectral analysis, such as frequency down-mixing.

Figure 5:
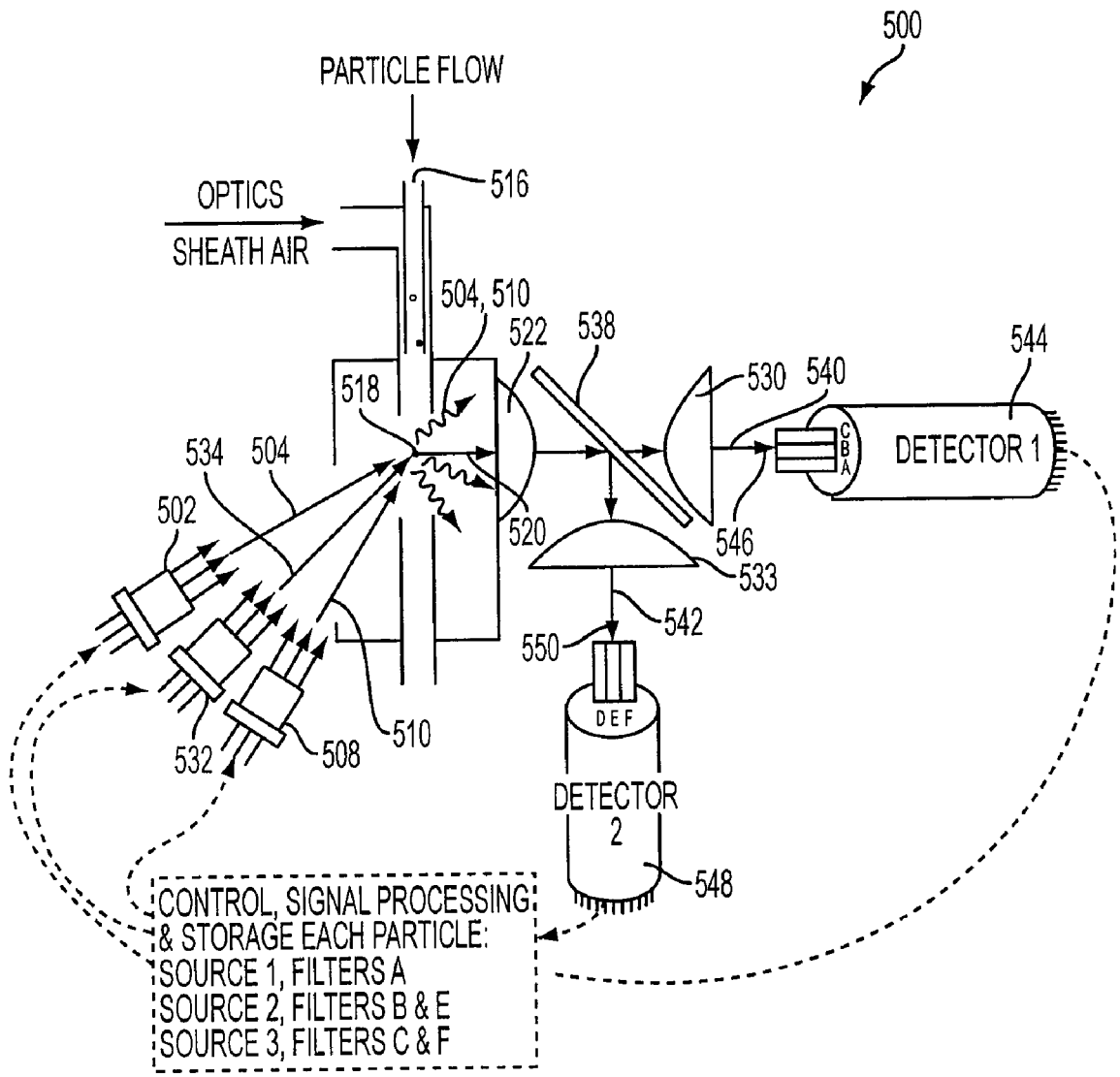
FIG. 5 is a schematic of a system according to a fifth embodiment of the invention.

FIG. 5 is a schematic of a multi-spectral aerosol particle measurement system 500 according to a fifth embodiment of the invention. As shown in FIG. 5, multi-spectral aerosol particle measurement system 500 may include a long emitter 502 emitting long wavelength radiation 504 (e.g., light at approximately 680 nm), a medium emitter 532 emitting medium wavelength radiation 534 (e.g., light at approximately 340 nm), and a short emitter 508 emitting short wavelength radiation 510 (e.g., light at approximately 280 nm).

In this embodiment, a particle 518 in a flowing fluid 516 is exposed to each of first, second, and third excitation wavelengths 504, 510 and 534 at different times because the excitation wavelengths are spatially separated. For example, as shown in FIG. 5, particle 518 is first exposed to excitation radiation 504, and then exposed to excitation radiation 534, and then exposed to excitation radiation 510. When particle 518 is exposed to excitation radiation, the particle may produce fluorescent radiation 520. A portion of the excitation radiation 504, 534, 510 may be scattered by particle 518 as well. A collimating lens 522 may be positioned to receive and collimate the elastic wavelengths (e.g., the scatter) and the inelastic wavelengths (e.g., fluorescent radiation 520).

A filter 538 (e.g., a dichroic filter or other filter) may be positioned to receive and transmit a first portion 540 of fluorescent radiation 520 and reflect a second portion 542 of fluorescent radiation 520. Additionally, filter 538 may also reflect a portion of the elastic radiation. Filter 538 may thus separate scattered long, medium, and short radiation 504, 534, 510 and fluorescent radiation 520 according to a threshold of wavelength.

A first focusing lens 530 may be positioned to receive and focus collimated first portion 540 of fluorescent radiation 520. A first detector 544 is positioned to receive the focused first portion 540 of fluorescent radiation 520. In one embodiment, first detector 544 is a photomultiplier with filters A, B, and C positioned in front of an input of detector 544.

In some embodiments, because excitation radiation 504, 510 and 534 is spatially separated in the region traversed by fluid 516, a particle in fluid 516 (e.g., particle 518) is sequentially exposed to the excitation radiations (e.g., particle 518 is first exposed to radiation 504, then radiation 534, then radiation 510). Preferably, filters A-C are disposed such that when particle 518 is exposed to excitation radiation 504, the elastic and inelastic radiation (or portion thereof) that is produced as a result of the exposure passes through filter-A only prior to reaching detector 544. Similarly, when particle 518 is exposed to excitation radiation 534, the elastic and inelastic radiation (or portion thereof) that is produced as a result of the exposure passes through only filter-B prior to reaching detector 544. Likewise, when particle 518 is exposed to excitation radiation 510, the elastic and inelastic radiation (or portion thereof) that is produced as a result of the exposure passes through only filter-C prior to reaching detector 544. In this way, the fluorescence intensity produced as a result of each excitation wavelength 504, 534 and 510 can be determined according to timing or sequence of signals output from detector 544.

A second focusing lens 533 may receive and focus collimated long, medium, and short wavelength radiation 504, 534, and 510 and second portion 542 of fluorescent radiation 520. A second detector 548 at second focus 550 may receive long, medium and short wavelength radiation 504, 534, and 510 and second portion 542 of fluorescent radiation 520. In one embodiment, second detector 548 is a photomultiplier with filters D, E, and F at an input to second detector 548.

In several embodiments, collimating lens 522 and focusing lenses 530 and 533 may be reflective or refractive optics (e.g., spherical, ellipsoidal, or parabolic reflectors). In several embodiments, an optical fiber or a light pipe may be used to transmit long and short wavelength radiation 504 and 510 to particle stream 516. In several embodiments, an optical fiber or a light pipe may be inserted in the collection path either before or after filter 538.

It may be advantageous to detect multiple emissions wavelengths with a single detector 544, even when two or more detectors 544 and 548 are used to detect multiple emissions from each excitation wavelength, since greater specificity can be obtained using multiple excitation and emission wavelengths.

In this embodiment, there are three light sources, long emitter 502, medium emitter 532, and short emitter 508, and one or more photo detectors 544 and 548. In this embodiment, one of long emitter 502, medium emitter 532, and short emitter 508 may be used to measure scattered light. As discussed above, particle 518 in fluid 516 may flow sequentially through long, medium, or short radiation 504, 534, 510.

In one embodiment, filter 538 is a band pass filter. In this embodiment, filter 538 is positioned to transmit selected wavelengths and to reflect other selected wavelengths. In one embodiment, scattered long, medium, or short radiation 504, 534, 510 and fluorescent radiation 520 is matched with various combinations of first and second detectors 544 and 548 and their-filters A, B, C, D, E, and F.

In one embodiment, short emitter 508 and filter A of first detector 544 are used to measure scattered light while second detector 548 is not used. In another embodiment, medium emitter 532 and filter B of first detector 544, as well as filter E of second detector 548 are used. In a third embodiment, long emitter 502 and filter C of first detector 544 is used with filter F of second detector 548.

Figure 6:
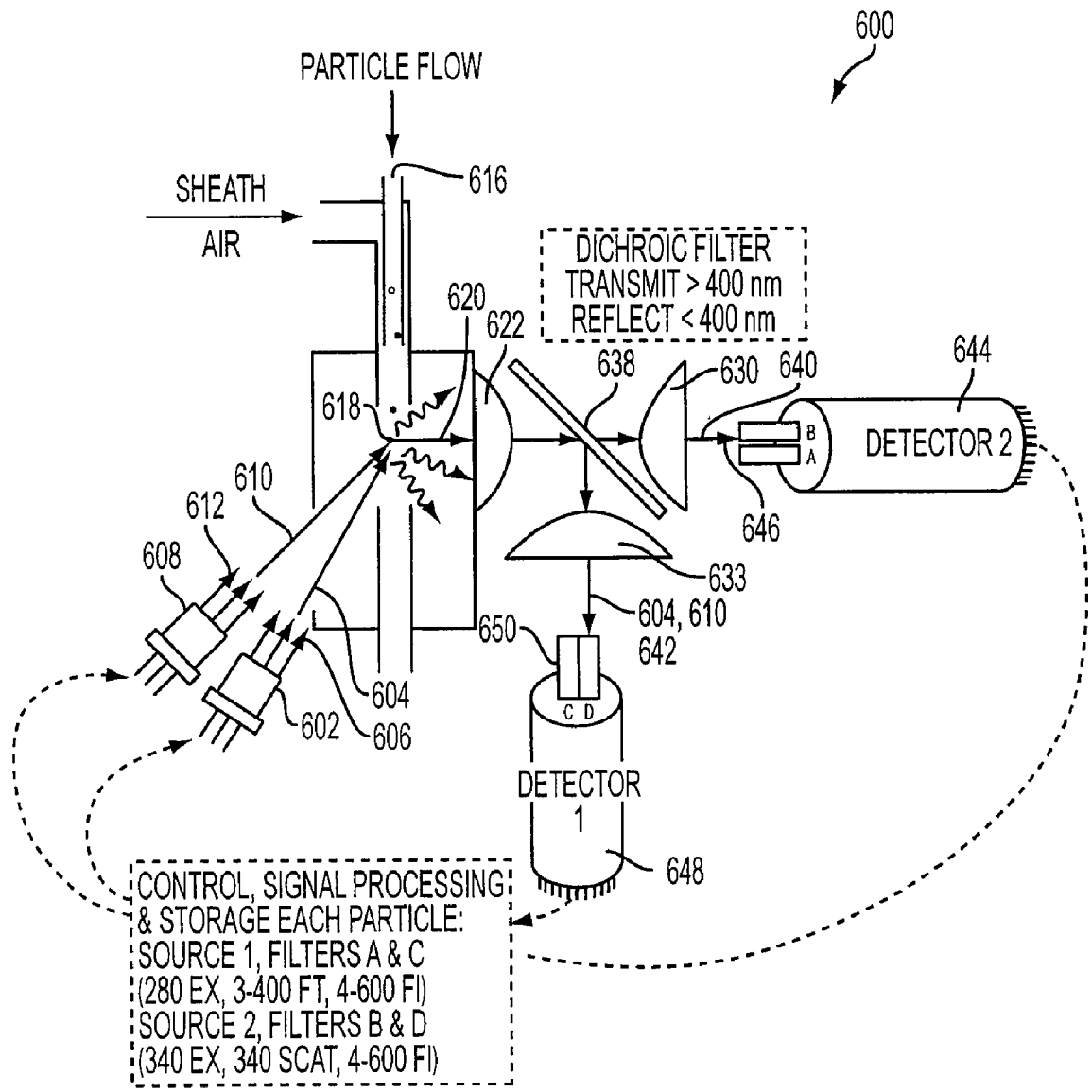
FIG. 6 is a schematic of a system according to a sixth embodiment of the invention.

FIG. 6 is a schematic of a multi-spectral aerosol particle measurement system 600 according to a sixth embodiment of the invention. As shown in FIG. 6, multi-spectral aerosol particle measurement system 600 may include a long emitter 602 emitting long wavelength radiation 604 and a short emitter 608 emitting short wavelength radiation 610.

In this embodiment, a flowing fluid 616 containing particles may intersect each of first and second directions 606 and 612. A particle 618 in fluid 616 intersecting first or second directions 606, 612 may produce fluorescent wavelength radiation 620 when exposed to long or short radiation 604, 610.

A portion of long or short radiation 604, 610 may be scattered by particle 618 as well. A collimating lens 622 may be positioned to receive and collimate scattered long and short radiation 604, 610 and fluorescent radiation 620.

A filter 638 (e.g., a dichroic filter or other filter) may be positioned to receive and reflect collimated long and short radiation 604, 610 and a first portion 642 of fluorescent radiation 620 and transmit a second portion 640 of fluorescent radiation 620. Filter 638 may thus separate scattered long and short radiation 604, 610 and fluorescent radiation 620 according to a threshold of wavelength.

A first focusing lens 633 may be positioned to receive and focus collimated long wavelength radiation 604 and short wavelength radiation 610, and first portion 642 of fluorescent radiation 620. A first detector 648 may be positioned at first focus 650 to receive long wavelength radiation 604 and short wavelength radiation 610, and first portion 642 of fluorescent radiation 620. In one embodiment, first detector 648 is a photomultiplier with filters C and D at an input to first detector 648.

A second focusing lens 630 may be positioned to receive and focus collimated second portion 640 of fluorescent radiation 620. A second detector 644 may be positioned at second focus 646 to receive second portion 640 of fluorescent radiation 620. In one embodiment, second detector 644 is a photomultiplier with filters A and B at an input to second detector 644.

In several embodiments, collimating lens 620 and focusing lenses 630 and 633 may be reflective or refractive optics (e.g., spherical, ellipsoidal, or parabolic reflectors). In several embodiments, an optical fiber or a light pipe may be used to transmit long and short wavelength radiation 604 and 610 to particle stream 616. In several embodiments, an optical fiber or a light pipe may be inserted in the collection path either before or after filter 638.

In one embodiment, long emitter 602 and short emitter 608 are used. In this embodiment, long wavelength radiation 604 from long emitter 602 may be detected at first detector 648 to measure light scatter. In this embodiment, short wavelength radiation 610 from short emitter 608 is detected at second detector 644 to measure fluorescence induced by short wavelength radiation 610.

In an alternative embodiment, long wavelength radiation 604 from emitter 602 may be detected by second detector 644 to measure fluorescence induced by long wavelength radiation 604. In this embodiment, short wavelength radiation 610 from emitter 608 is detected at first detector 648 to measure light scatter.

Figure 7:
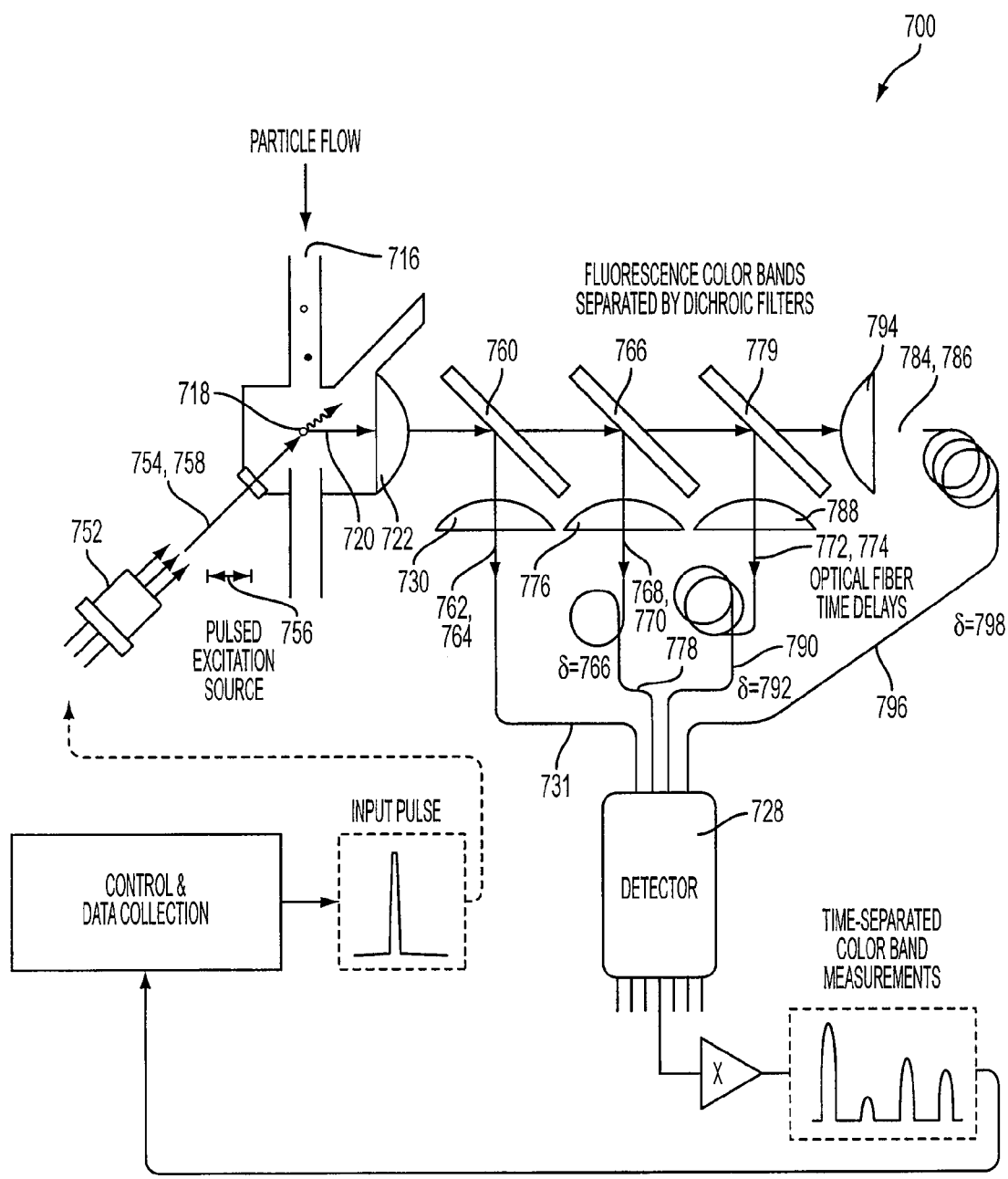
FIG. 7 is a schematic of a system according to a seventh embodiment of the invention.

FIG. 7 is a schematic of a multi-spectral aerosol particle measurement system 700 according to a seventh embodiment of the invention. As shown in FIG. 7, a multi-spectral aerosol particle measurement system 700 may include a pulsed emitter 752 emitting a pulse 754 of radiation for a duration 756 in a direction 758. The radiation output from emitter 752 may have a wavelength in the range of 200-700 nm.

In one embodiment, a fluid flow 716 may intersect direction 758. A particle 718 in fluid flow 716 may be exposed to radiation pulse 754 and produce fluorescent radiation 720. Fluorescent radiation 720 may include high, medium and low fluorescent radiation (i.e., fluorescent radiation 720 may include different wavelengths of radiation). Particle 718 may also scatter some of radiation pulse 754. The scattered radiation may include high, medium and low scattered radiation (i.e., the scattered radiation may include different wavelengths of radiation).

A collimating lens 722 may be positioned to receive and collimate the scattered radiation and fluorescent radiation 720. A filter 760 (e.g., a dichroic filter, prism, grating or other filter) may be configured to spatially separate high scattered radiation 762 and high fluorescent radiation 764 from medium and low scattered radiation 768, 772 and medium and low fluorescent radiation 770, 774 according to a threshold of wavelength.

A focusing lens 730 may be positioned to receive and focus only high scattered radiation 762 and high fluorescent radiation 764. An optical fiber 731 (or other transmission path) may be positioned at a focus of focusing lens 730 to receive focused radiation 762 and 764. Optical fiber 731 may transmit radiation 762 and 764 to a detector 728. In one embodiment, detector 728 is a photomultiplier.

A filter 766 may separate medium scattered radiation 768 and medium fluorescent radiation 770 from low scattered radiation 772 and low fluorescent radiation 774 according to a threshold of wavelength. A focusing lens 776 may be positioned to receive and focus only medium scattered radiation 768 and medium fluorescent radiation 770. An optical fiber 778 may be positioned at a focus of focusing lens 776 to receive focused radiation 768, 770. Optical fiber 778 may transmit radiation 768, 770 to detector 728. Radiation 768, 770 may be delayed a period of time 766 by optical fiber 778.

In one embodiment, optical fiber 778 is longer than optical fiber 731. In this embodiment, radiation 768, 770 require a longer period of time to traverse optical fiber 778 than radiation 762, 764 require to traverse optical fiber 731.

A filter 779 may separate low scattered radiation 772 and low fluorescent radiation 774 from residual scattered radiation 784 and residual fluorescent radiation 786 according to a threshold of wavelength. A focusing lens 788 may be positioned to receive and focus only radiation 772, 774. An optical fiber 790 may be placed at a focus of focusing lens 788 to receive focused radiation 772, 774. Optical fiber 790 may delay radiation 772, 774 a period of time 792 and transmit radiation 772, 774 to detector 728.

In one embodiment, optical fiber 790 is longer than optical fiber 778. In this embodiment, radiation 772, 774 require a longer period of time to traverse optical fiber 790 than radiation 768, 770 require to traverse optical fiber 778.

A focusing lens 794 may receive and focus residual radiation 784, 786. An optical fiber 796 may receive focused radiation 784, 786. Optical fiber 796 may delay radiation 784, 786 a period of time 798 and may transmit radiation 784, 786 to detector 728.

In several embodiments, collimating lens 722 and focusing lenses 730, 776, and 788 may be reflective or refractive optics (e.g., spherical, ellipsoidal, or parabolic reflectors). In several embodiments, an optical fiber or a light pipe may be used to transmit pulse 754 to particle stream 716. In several embodiments, an optical fiber or a light pipe may be inserted in the collection path either before or after each high, medium, or low filter 760, 766, and 779.

In one embodiment, pulsed emitter 752 may be a pulsed laser with a pulse duration 756. In this embodiment, duration 756 may be shorter than a transit time of pulse 754 down a practical length of optical fiber.

In one embodiment, pulsed emitter 752 may be used with a particle detection system that includes low-cost visible or near infrared light source. In this embodiment, pulsed emitter 752 is configured so that the generated radiation pulse 754 passes through a predetermined region of space, and the light source in combination with a detector are used to (a) detect when a particle in fluid 716 is within the predefined region or about to enter the region and (b) trigger pulsed emitter 752 to generate a radiation pulse 754 when the particle is detected to be within the predefined region or about to enter the region so that the particle will likely be illuminated by the generated radiation pulse 754.

As discussed above, scattered radiation and fluorescent radiation 720 are separated into high, medium, and low portions 762, 768, 772 and high, medium, and low portions 764, 770, 774, respectively. Each high, medium, and low portions 762, 768, 772 and high, medium, and low portions 764, 770, 774 are focused into separate optical fibers 731, 778, and 790 (or other transmission paths).

Optical fibers 731, 778, and 790 preferably have different optical path lengths. The lengths can be selected so that each of high, medium, and low scattered radiation 762, 768, 772 and high, medium, and low fluorescent radiation 764, 770, 774 are separated in time when arriving at detector 728.

Since each of high, medium, and low portions 762, 768, 772 and high, medium, and low portions 764, 770, 774 arrive separately, the amplitudes of high, medium, and low portions 762, 768, 772 and high, medium, and low portions 764, 770, 774 can be measured individually based on their times of arrival after pulsed emitter 752 emits pulse 754.

For example, if the duration 756 of pulse 754 is 2 nS, which is typical of some pulsed UV lasers, it would be desirable to have 5 to 10 nS elapse between the times separated color bands arrive at detector 728. The time T for pulse 754 to travel down an optical fiber is given by:

$T = L/(c/n)$ where $L$=geometric fiber length, $c$=speed of light in vacuum=$3 \times 10^8$ m/s, and $n$=refractive index of optical fiber.

Thus, for 10 nS time separation with a fiber refractive index of 1.5, the geometric length of fiber required is 2 meters. Thus in FIG. 7, detector 728 may use optical fiber lengths of 0.1 m for optical fiber 731, 2.1 m for optical fiber 778, 4.1 m for optical fiber 790, and 6.1 m for optical fiber 796.

In one embodiment, an intensity of a first optical signal at detector 728 may be substantially different than that of a second optical signal reaching detector 728. In this embodiment, a dynamic range between first and second optical signals at detector 728 may be too great to cover by conventional signal processing means. Accordingly, an optical density, or transmission, of each of high, medium, and low filters 760, 766, and 778 may be adjusted so that all signal intensities are within a useful range. In addition to (or as an alternative) the following techniques may be used alone or in combination: a gain of detector 728 may be switched rapidly to accommodate the varying incoming radiation; detector 728 may be switched rapidly between predetermined voltages on a photomultiplier dynode chain; detector 728 may be switched rapidly between cathode-to-dynode voltages; detector 728 may be switched rapidly between individual dynode-to-dynode voltages; detector 728 may be an avalanche photo detector in which a bias voltage is changed; detector 728 may use logarithmic amplification; an incoming optical signal may be processed on multiple channels at once.

Figure 9:
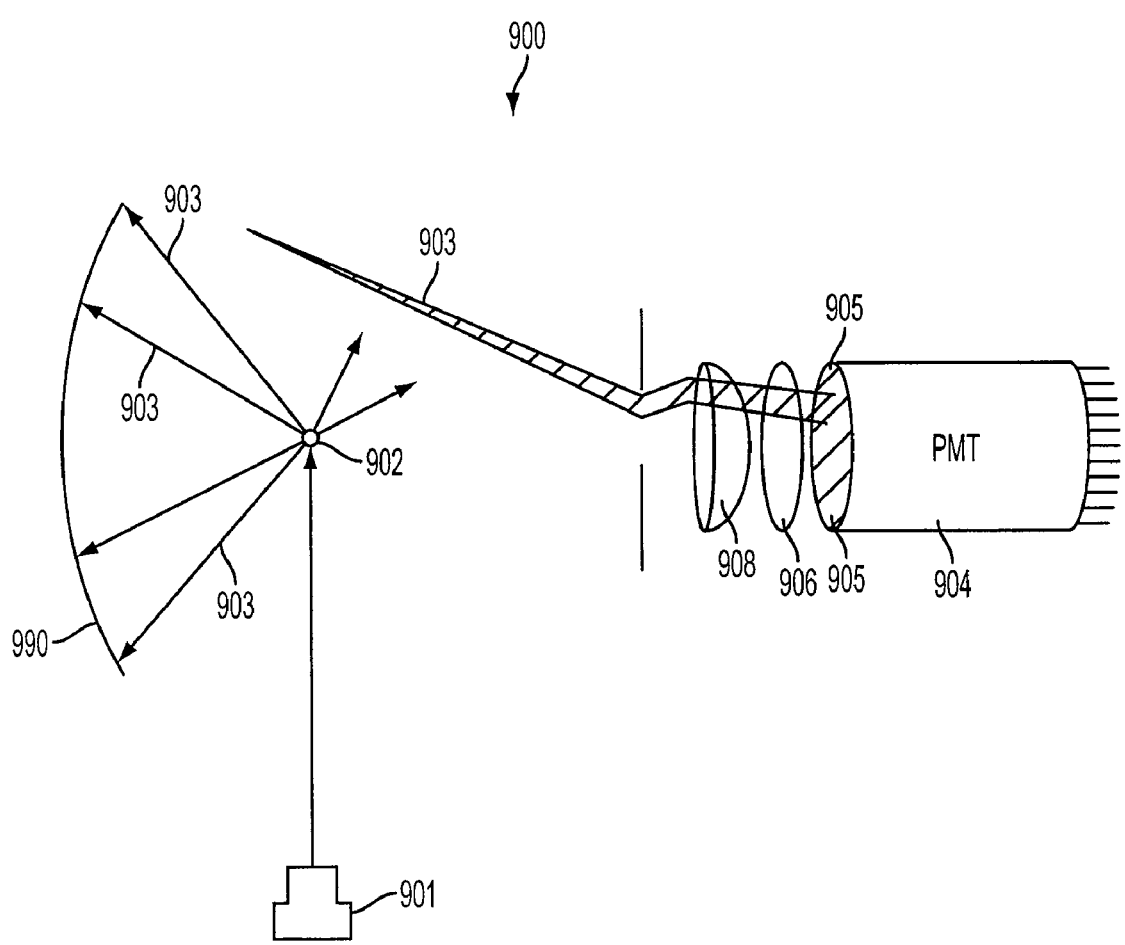
FIG. 9 is a schematic of a system according to an eighth embodiment of the invention.

FIG. 9 is a schematic of a multi-spectral aerosol particle measurement system 900 according to an eighth embodiment of the invention. As described below, system 900 uses a single detector (e.g., a single photomultiplier tube (PMT)) to detect multiple fluorescence signals (i.e., signals having different wavelengths) from an airborne particle. This provides a lower cost design, and contrasts with conventional designs that use a PMT for each fluorescence wavelength detected.

As shown in FIG. 9, a multi-spectral aerosol particle measurement system 900 may include: one or more emitters 901 for illuminating a particle of interest 902, a single detector 904 (e.g., a single PMT) for detecting radiation 903 emitted from the particle as a result of the particle being illuminated by the emitter 901, and a dual band filter 906 disposed in front of the sensitive region 905 of the detector 904 to prevent unwanted radiation from reaching the detector's sensitive region 905. System 900 may also include a reflector 990 for reflecting light towards detector 904 and a relay lens 908 for reducing the angle of incidence of the light reaching the filter 906—this may be advantageous since the optical response of some filters (e.g., thin film optical interference filters) varies with the angle of incidence.

Many of the above described embodiments illustrate systems in which a particle passes sequentially through two or more light sources such that the fluorescent light resulting from each source is separated not only in time, but also in space onto two or more distinct regions of a detector, with a separate filter for each region. The embodiment shown in FIG. 9 is different in that the fluorescence signals from a given particle are separated in time, but the optical design constraint of spatial separation is not required.

Spatial separation is not required because filter 906 blocks at least two different wavelength bands. For example, in one embodiment filter 906 is configured such that it functions as (1) a long pass filter (e.g., blocking wavelengths less than 280 nm while passing longer wavelengths such as the 320-370 and 420-650 emission wavelengths) and (2) a band rejection filter that filters all wavelengths in a certain band (e.g., all wavelengths between 380 and 410). This feature is illustrated in FIG. 10.

This feature of filter 906 enables one to use a single detector to measure two or more wavelength regions of fluorescence of an airborne particle to discriminate better between threat particles and benign background particles that may have some fluorescent properties.

To accomplish this using system 900, a user would (a) use an emitter to illuminate a particle of interest for a generally short, predetermined period of time using a first wavelength (e.g., 280 nm, which causes the biological component tryptophan to fluoresce from approximately 320 to 370 nm), which first wavelength of light is blocked by filter apparatus 906 from reaching detector 904, while the particle is in the field of view of detector 904, (b) after illuminating the particle, obtaining output from the detector, which output is a function of the intensity of fluorescence wavelengths that were emitted from the particle as a result of the particle being illuminated by the first wavelength and that were not blocked by filter apparatus 906, (c) after step (b) and while the particle is still within the detector's field of view, use a second emitter or the same emitter to illuminate the particle for a generally short, predetermined period of time using a second wavelength (e.g., 395 nm, which causes the biological components NAD(P)H and flavins to fluoresce from approximately 420 to 650 nm), which second wavelength of light is also blocked by filter apparatus 906 from reaching detector 904, and (d) after step (c), obtaining the output from the detector, which output is a function of the intensity of fluorescence wavelengths emitted from the particle as a result of the particle being illuminated by the second wavelength that were not blocked by filter apparatus 906. Accordingly, system 900 enables one to determine a particle's reaction to at least two distinct wavelengths of light using only a single PMT and within a very short period of time (i.e., before the particle moves out of the detectors field of view).

Figure 10:
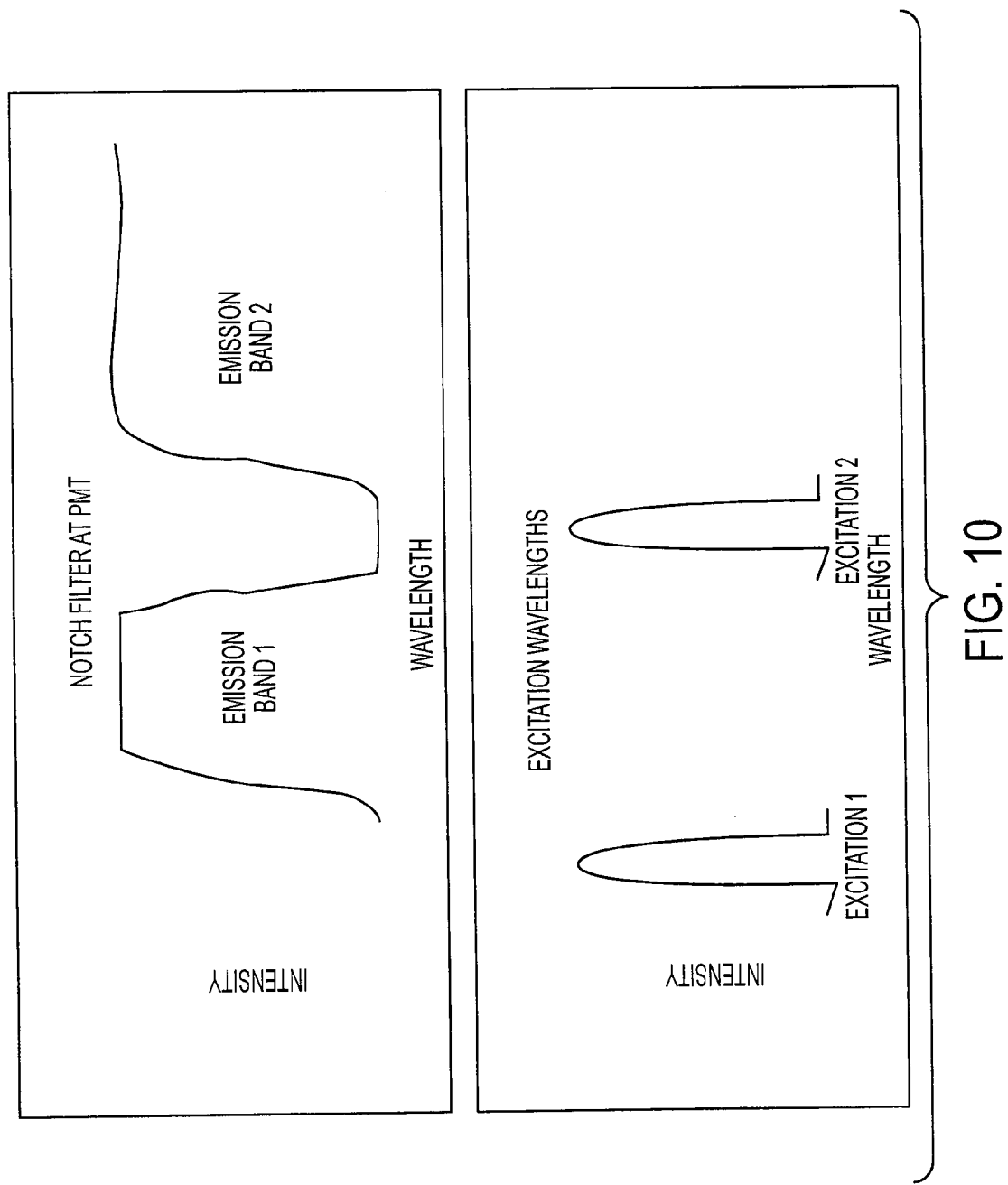
FIG. 10 illustrates a filter response.

The above is illustrated in FIG. 10, which shows (1) energy being emitted at a first wavelength, which first wavelength is blocked by filter 906 and (2) energy being emitted at a second wavelength, which second wavelength is also blocked by filter 906.

Fabrication of filter 906 can be readily accomplished with conventional fabrication technologies, since it consists of a combination of standard filter designs. Specifically, as described above, filter 906 can be achieved by combining two filter functions: (1) a long pass filter and (2) a band rejection filter. The combination can be achieved in several ways, such as by: (a) using two separate filters in sequence (e.g., a long pass filter followed by a band rejection filter or vice-versa), (b) using a single filter substrate coated on one side to accomplish function (1) and on the other side accomplish function (2), (c) adding a coating to accomplish function (2) onto a bulk glass filter, such as Schott WG320, that accomplishes function (1), or (d) adding a coating to accomplish function (1) onto a filter hat accomplishes function (2).

Another useful method for characterizing threat particles relates to techniques for the analysis of data from a number of particles in order to determine when a target for recognition, such as a bio-aerosol threat, is present. In several embodiments, a variety of pattern classification and recognition methods may be applied to the problem of identifying targets within background particles, such as correlation, principal component analysis, support vector machines, wavelet transforms and multi-dimensional Fourier transforms, and other data mining and pattern recognition methods as may be found in literature.

In one embodiment, particles are measured for a fixed time interval, and the accumulated particle measurements for each time interval are analyzed for the potential presence of threat particles. For each data interval, the degree of pattern match, or the percentage of particles in a target region in data space relative to particles in non-target data space, are tracked versus time and alarm decisions are based on statistically significant increases in the degree of pattern match or percentage.

Since the concentration of background particles and potential threat particles may vary over many (5-6) orders of magnitude, this means that at times of low particle concentration there is relatively large variability in the analysis due to counting statistical variations, while at times of high concentration there are many more particles than are needed for good analysis.

In one embodiment, analysis of the particle stream is performed at variable time intervals but at fixed particle count intervals. In this embodiment, sufficient particle counts may be obtained to make a valid determination of the presence of a biological threat at low particle concentrations. In this embodiment, a determination of the presence of a biological threat may also be made in the shortest possible period while particle concentrations are high Further, many analysis methods require normalization of the particle data. In this embodiment, sampling for a fixed number of particle counts may eliminate the normalization step.

In another embodiment, the data signature of threat or targeted particle is predetermined. In this embodiment, particles can be sampled until a statistically valid number of such predetermined target particle measurements are acquired. This provides for a fast response while assuring that statistical validity is obtained for the decision of whether the target is present.

The methods described above may be performed with continuous wave (CW) excitation sources or pulsed excitations sources. For example, in the systems shown in FIGS. 2, 5 and 6, the excitation source(s) may be CW excitation sources or pulsed excitations sources. When pulsed sources are used, they may be pulsed or turned on during the particle transit through the location of that source, based on timing from prior sensing of the particle, such as from an illumination from an energy source and detection of the scattered energy. The determination of transit may be based either measurement of particle velocity, or on maintaining a controlled flow velocity of the aerosol such that the transit time from the prior sensing to the excitation is known. Use of dichroic filters to combine sources is also an option.

As particles pass individually through one or more excitation sources, the wavelength(s) of a filter or filters may be changed at a rate slower than the transit time of an individual particle, such that a series of particles are sensed each detection wavelength or combination of wavelengths. (For example, individual particles could be sensed for n seconds at filter waveband or waveband combination 1, for m seconds and filter waveband or waveband combination 2, etc.) In this way, over the time period of a release of particles of interest for detection, a subset of particles will be measured with each filter waveband of interest.

Methods for changing filters may include: mechanical repositioning of fixed bandpass filters, tunable gratings, prisms, etalons, and liquid crystal tunable filter, micro-machined tunable gratings, etc.

While various embodiments/variations of the present invention have been described above, it should be understood that they have been presented by way of example only, and not limitation. Thus, the breadth and scope of the present inven-

What is claimed is:

1. An aerosol detector system, comprising:
   a detector having a detector input and a field of view;
   an emitter apparatus configured to emit into a region of space within the field of view of the detector different wavelengths of excitation energy at different times such that a particle located within the field of view of the detector may be exposed to said different wavelengths of excitation energy at said different times while fluorescent light from the particle remains located at substantially the same position in space on the detector input at each of the different times;
   a reflector positioned such that the region of space is between the reflector and the detector and configured such that the reflector reflects light toward the detector; and
   a filter disposed in front of the detector input, wherein the filter is configured to filter a first band of wavelengths and a second band of wavelengths.

2. The detector system of claim 1, wherein the first band of wavelengths includes wavelengths less than a first wavelength and the second band of wavelengths includes wavelengths between a second wavelength and a third wavelength.

3. The detector apparatus of claim 2, wherein the filter comprises a single filter substrate having a first filter coating on one side and a second filter coating on the other side, wherein the first filter coating filters wavelengths less than the first wavelength, and the second filter coating filters wavelengths less than the third wavelength, but not less than the second wavelength.

4. The detector system of claim 2, wherein the first wavelength is less than 320 nm.

5. The detector system of claim 4, wherein the emitter apparatus comprises an emitter operable to emit excitation energy having a wavelength of less than 320 nm.

6. The detector apparatus of claim 5, wherein the emitter is a laser configured to output a coherent beam of light having a wavelength of less than 320 nm.

7. The detector system of claim 5, wherein the second wavelength is greater than 370 nm and the third wavelength is less than 420 nm.

8. The detector system of claim 7, wherein the emitter apparatus comprises: (a) a first emitter configured to emit excitation energy having a wavelength of less than 320 nm and (b) a second emitter configured to emit excitation energy having a wavelength of less than 420 nm but greater than 370 nm.

9. The detector apparatus of claim 1, wherein the filter comprises: (a) a long pass filter coated with a band rejection filter coating and/or (b) a band rejection filter coated with a long pass filter coating.

10. The detector system of claim 1, wherein the filter comprises: a long pass filter and a band rejection filter.

11. The detector system of claim 1, further comprising a relay lens positioned in front of the filter.

12. An aerosol detector system, comprising:
    detecting means for detecting emissions from the particle, said detecting means having a field of view;
    emitting means for emitting into a region of space within the field of view of the detector different wavelengths of excitation energy at different times such that a particle located within the field of view of the detector may be exposed to said different wavelengths of excitation energy at said different times while fluorescent light from the particle remains located at substantially the same position in space on the detector input at each of the different times;
    a reflecting means positioned such that the region of space is between the reflecting means and the detecting means and configured such that the reflecting means reflects light toward the detecting means; and
    a filter disposed in front of an input of the detecting means for filtering at least two different wavelength bands.

13. The detector system of claim 12, wherein the filter comprises: (a) a long pass filter that filters wavelengths less than a first wavelength, and (b) a band rejection filter that filters wavelengths between a second and a third wavelength.

14. The detector system of claim 13, wherein the first wavelength is less than 320 nm.

15. The detector system of claim 14, wherein the emitting means comprises an emitter operable to emit excitation energy having a wavelength of less than 320 nm.

16. The detector system of claim 15, wherein the second wavelength is greater than 370 nm and the third wavelength is less than 420 nm.

17. The detector system of claim 16, wherein the means for emitting comprises: (a) a first emitter configured to emit excitation energy having a wavelength of less than 320 nm and (b) a second emitter configured to emit excitation energy having a wavelength of less than 420 nm but greater than 370 nm.

18. The detector system of claim 12, wherein the filter comprises a single filter substrate having a first filter coating on one side and a second filter coating on the other side.

19. The detector system of claim 15, wherein the first filter coating filters wavelengths less than a first wavelength, and the second filter coating filters wavelengths less than a second wavelength.

20. The detector system of claim 12, wherein the filter comprises a long pass filter coated with a band rejection filter coating.

21. The detector apparatus of claim 12, wherein the filter comprises a band rejection filter coated with a long pass filter coating.

22. The detector system of claim 12, further comprising means for reducing the incidence of light reaching the filter means.

23. In an aerosol detector system comprising a detector having a detector input and a field of view and a filter disposed in front of the detector input, wherein the filter is configured to filter a first band of wavelengths and a second band of wavelengths, a method comprising:
    (a) while an aerosol is positioned within the field of view of the detector in a region of space between the detector and a reflector, illuminating the aerosol using a first wavelength of light; and
    (b) after performing step (a) and while the aerosol is still positioned within the field of view of the detector in the same region of space between the detector and the reflector, illuminating the aerosol using a second wavelength of light.

24. The method of claim 23, wherein the step of illuminating the aerosol using the first wavelength of light consists of illuminating the aerosol with the first wavelength of light for a predetermined generally short period of time.

25. The method of claim 24, wherein the step of illuminating the aerosol using the second wavelength of light consists of illuminating the aerosol with the second wavelength of light for a predetermined generally short period of time.

26. The detector system of claim 25, wherein the first band of wavelengths includes the first wavelength and the second band of wavelengths includes the second wavelength.

27. The method of claim 26, wherein the first wavelength is less than 320 nm.

28. The method of claim 27, wherein the second wavelength is between 370 nm and 420 nm.

29. The method of claim 28, further comprising obtaining a signal output from the detector and processing the signal, wherein the signal corresponds to the intensity of light emitted from the aerosol in response to the aerosol being illuminated by the first wavelength.

30. The method of claim 29, wherein the light emitted from the aerosol in response to the aerosol being illuminated by the first wavelength passes through said filter prior to reaching the input of the detector.

31. The method of claim 30, further comprising obtaining a second signal output from the detector and processing the second signal, wherein the second signal corresponds to the intensity of light emitted from the aerosol in response to the aerosol being illuminated by the second wavelength.

32. The method of claim 31, wherein the light emitted from the aerosol in response to the aerosol being illuminated by the second wavelength passes through said filter prior to reaching the input of the detector.

33. The method of claim 32, further comprising determining whether the aerosol is a harmful aerosol based, at least in part, on said first signal and said second signal.

34. The method of claim 32, further comprising characterizing the aerosol based, at least in part, on said first signal and said second signal.

* * * * *

UNITED STATES PATENT AND TRADEMARK OFFICE
Certificate

Patent No. 7,525,660 B2                                                            Patented: April 28, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: George W. Gigioli, Brookeville, MD (US); David W. Bope, Burtonsville, MD (US); Peter P. Hairston, Severna Park, MD (US); Edward A. Miller, Severna Park, MD (US); and Carl B. Freidhoff, New Freedom, PA (US).

Signed and Sealed this Twenty-seventh Day of July 2010.

Gregory J. Toatley, Jr.
*Supervisory Patent Examiner*
Art Unit 2877
Technology Center 2800